United States Patent [19]
Lazzara et al.

[11] Patent Number: 5,709,547
[45] Date of Patent: *Jan. 20, 1998

[54] DENTAL IMPLANT FOR ANCHORAGE IN CORTICAL BONE

[75] Inventors: Richard J. Lazzara; Keith D. Beaty, both of West Palm Beach, Fla.

[73] Assignee: Implant Innovations, Inc., Palm Beach Gardens, Fla.

[*] Notice: The term of this patent shall not extend beyond the expiration date of Pat. No. 5,695,336.

[21] Appl. No.: 601,840

[22] Filed: Feb. 15, 1996

Related U.S. Application Data

[63] Continuation of Ser. No. 239,122, May 6, 1994, abandoned, which is a continuation-in-part of Ser. No. 845,138, Mar. 3, 1992, Pat. No. 5,364,268.

[51] Int. Cl.$^6$ .................................................. A61C 8/00
[52] U.S. Cl. .................................................. 433/174
[58] Field of Search ........................... 433/173, 174, 433/175, 176

[56] References Cited

U.S. PATENT DOCUMENTS

| | | | |
|---|---|---|---|
| 2,112,007 | 3/1938 | Adams | 32/2 |
| 3,067,740 | 12/1962 | Haboush | 128/92 |
| 3,488,779 | 1/1970 | Christensen | 3/1 |
| 3,846,846 | 11/1974 | Fischer | 3/1 |
| 4,145,764 | 3/1979 | Suzuki et al. | 3/1.9 |

(List continued on next page.)

FOREIGN PATENT DOCUMENTS

| | | |
|---|---|---|
| 0 111134 | 6/1984 | European Pat. Off. . |
| 0 126624 | 11/1984 | European Pat. Off. . |
| 0 139052 | 5/1985 | European Pat. Off. . |
| 0 216031 | 4/1987 | European Pat. Off. . |
| 0 237505 | 9/1987 | European Pat. Off. . |
| 0 288702 | 11/1988 | European Pat. Off. . |
| 0 530160 | 3/1993 | European Pat. Off. . |
| 3043336 | 11/1981 | Germany . |
| 332486 | 2/1971 | Sweden . |
| 1 291 470 | 10/1972 | United Kingdom . |

OTHER PUBLICATIONS

Bone Screw Technical Information by Richards Technical Publication (1980, pp. 1–14).
Sustain®, H–A Bointegrated Dental Implant System, 1991.
Steri–Oss, The Future of Implant Dentistry, 1990.
OsteoImplant Corp., 1990.
Southern Implants, B–Series, Dental Implants, Apr. 1, 1993.
Interpore, Price and Data Sheet, 1989.
Imtec, Hexed Head Implant Systems, Spring 1993 Catalog, 1993.
Implant Support Systems, Inc., Products for diagnosis, surgery, restoration, laboratory, 1989.
Implamed, The Source, Nov. 1992.
Dentsply, Restorative Manual, 1992.
Dentsply, Price List, Jun. 1, 1992.
Core–Vent Corporation "Spectra System: The Only Complete System of Osseointegrated Implants", 1990.
Core–Vent Corporation "Diagnosis And Treatment Planning Guidelines", Oct. 12, 1989.

(List continued on next page.)

*Primary Examiner*—Cary E. O'Connor
*Attorney, Agent, or Firm*—Arnold, White & Durkee

[57] ABSTRACT

A dental implant intended for installation in maxillary and mandibular posterior regions where bone is cancellous internally and cortical externally characterized by labial and buccal cortical plates bounding a relatively large body of cancellous bone. The body of the implant fixture has a width dimension that is substantially the same as the distance between the labial and buccal cortical plates in the site of installation. When installed in that site the implant makes bone-to-implant contact with both of the plates simultaneously. The length of this implant fixture is limited so that when so installed it does not make contact with the mandibular canal or the sinus cavity.

33 Claims, 2 Drawing Sheets

U.S. PATENT DOCUMENTS

| | | | |
|---|---|---|---|
| 4,414,966 | 11/1983 | Stednitz | 128/92 B |
| 4,463,753 | 8/1984 | Gustilo | 128/92 B |
| 4,466,796 | 8/1984 | Sandhaus | 433/173 |
| 4,468,200 | 8/1984 | Münch | 433/174 |
| 4,480,997 | 11/1984 | Deutsch et al. | 433/211 |
| 4,484,570 | 11/1984 | Sutter et al. | 128/92 D |
| 4,495,664 | 1/1985 | Blanquaert | 3/1.913 |
| 4,511,335 | 4/1985 | Tatum, Jr. | 433/173 |
| 4,535,487 | 8/1985 | Esper et al. | 623/22 |
| 4,537,185 | 8/1985 | Stednitz | 128/92 B |
| 4,668,191 | 5/1987 | Plischka | 433/174 |
| 4,713,003 | 12/1987 | Symington et al. | 433/173 |
| 4,713,004 | 12/1987 | Linkow et al. | 433/173 |
| 4,722,688 | 2/1988 | Lonca | 433/173 |
| 4,738,623 | 4/1988 | Driskell | 433/173 |
| 4,826,434 | 5/1989 | Krueger | 433/174 |
| 4,851,008 | 7/1989 | Johnson | 623/16 |
| 4,854,872 | 8/1989 | Detsch | 433/173 |
| 4,863,383 | 9/1989 | Grafelmann | 433/174 |
| 4,878,915 | 11/1989 | Brantigan | 623/17 |
| 4,915,628 | 4/1990 | Linkow et al. | 433/173 |
| 4,932,868 | 6/1990 | Linkow et al. | 433/174 |
| 4,934,935 | 6/1990 | Edwards | 433/173 |
| 4,960,381 | 10/1990 | Nizmick | 433/174 |
| 4,978,350 | 12/1990 | Wagenknecht | 606/72 |
| 4,988,299 | 1/1991 | Branemark | 433/174 |
| 5,015,186 | 5/1991 | Detsch | 433/173 |
| 5,049,073 | 9/1991 | Lauks | 433/173 |
| 5,061,181 | 10/1991 | Nizmick | 433/174 |
| 5,064,425 | 11/1991 | Branemark et al. | 606/72 |
| 5,076,788 | 12/1991 | Nizmick | 433/173 |
| 5,078,607 | 1/1992 | Nizmick | 433/174 |
| 5,100,323 | 3/1992 | Friedman et al. | 433/173 |
| 5,135,394 | 8/1992 | Hakamatsuka et al. | 433/173 |
| 5,188,800 | 2/1993 | Green, Jr. et al. | 422/23 |
| 5,209,659 | 5/1993 | Friedman et al. | 433/173 |
| 5,254,005 | 10/1993 | Zuest | 433/173 |
| 5,269,685 | 12/1993 | Jörnéus et al. | 433/174 |
| 5,312,256 | 5/1994 | Scortecci | 433/174 |
| 5,324,199 | 6/1994 | Branemark | 433/174 |
| 5,435,723 | 7/1995 | O'Brien | 433/174 |
| 5,449,291 | 9/1995 | Lueschen et al. | 433/173 |
| 5,591,029 | 1/1997 | Zuest | 433/174 |

OTHER PUBLICATIONS

Core–Vent "Les Systemes Implantaires", Jan. 10, 1990.

"Cemented Abutments for Crown and Bridge", Date Prior to Filing Date.

Core–Vent Corporation "Order Forms", Sep. 1989.

Core–Vent Corporation "The Longitudinal Clinical Efficacy of Core–Vent Dental Implants; A Five–year Study", Journal of Oral Implantology, vol. XV, No. 2, 1989.

Ledermann, Frischherz, and Markwalder, "The Ha–Ti Implant", Schweiz Monatsschr Zahnmed, vol. 101, May 1991.

Driskell Bioengineering, "The DB Precision Implant System 1000 Series", 1986.

"Ha–Ti Implant Short Neck Measuring Template," Mathys Dental LTD, Aug. 1992.

Langer et al., "The Wide Fixture: A Solution for Special Bone Situations and a Rescue for the Compromised implant. Part 1," The International Journal of Oral & Maxillofacial Implants, pp. 400–408, vol. 8, No. 4, 1993 (9 pages).

Academy of Osseointegration Program, Mar. 4–6, 1993, cover page and pp. 32–33.

"Titanodont™ Subcortical Implant System," Miter, Inc.

U. Lekholm, "The Branemark Implant Technique: A Standardized Procedure Under Continuous Development," 2nd Int. Tissue International Congress, Rochester, Minnesota, Sep. 1990, pp. 194–199.

Jaffin & Berman "The Excessive Loss of Branemark Fixtures in Type IV Bone: A 5–Year Analysis," J. Peridontal, 1991, 62:2–4.

Langer, B. et al., "Osseointegration: Its Impact On the Interrelationship of Periodontics And Restorative Dentistry: Part 1," The International Journal of Periodontics & Restorative Dentistry, vol. 9, No. 2, 1989 at pp. 85 to 105.

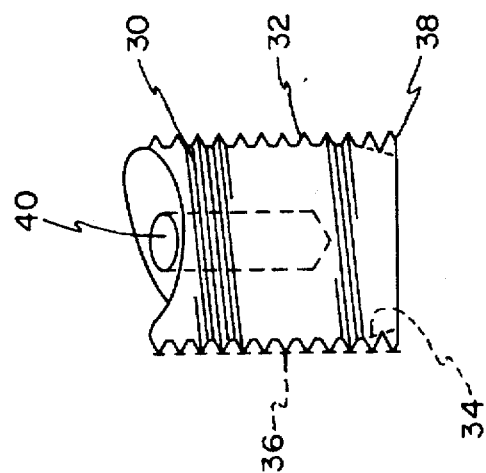
FIG. 3
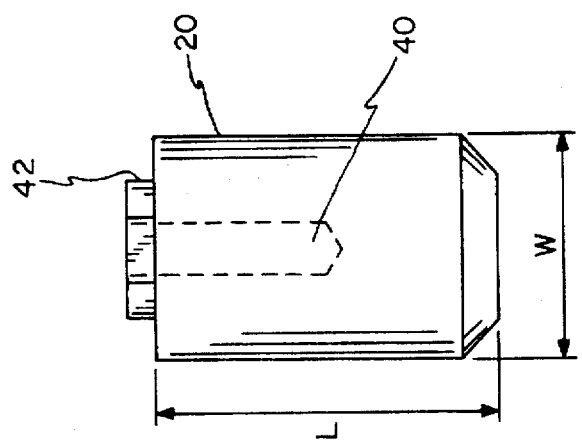
FIG. 2
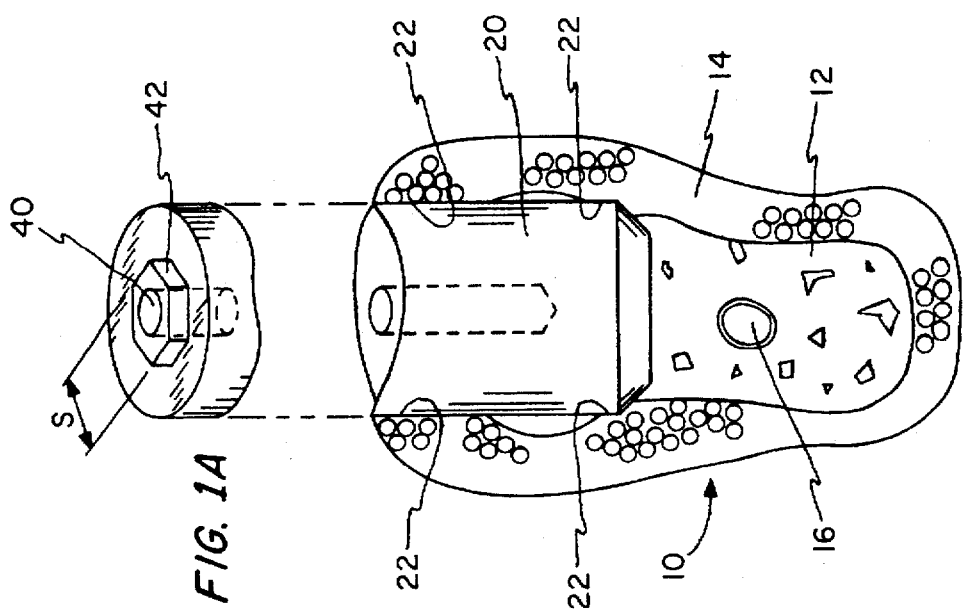
FIG. 1A
FIG. 1

DENTAL IMPLANT FOR ANCHORAGE IN CORTICAL BONE

This application is a file wrapper continuation of application Ser. No. 08/239,122, filed May 6, 1994, now abandoned, which is a continuation-in-part of application Ser. No. 07/845,138 filed Mar. 3, 1992 and issued as U.S. Pat. No. 5,364,268.

BACKGROUND OF THE INVENTION

This invention relates to dental implants, particularly to implants intended for installation in the maxillary and mandibular posterior regions where bone is cancellous internally and cortical externally.

As it has developed to the present time, the technology of dental implants preferentially employs cylindrical implants, some externally threaded, and some not threaded, but all being much longer than they are wide with the ratio of length to width being about 1.8 to 5.3, for example. This may be due primarily to the fact that early successes were experienced with installation in the anterior area of dental arches. Thus, dental implants commonly available at the present time have lengths ranging up to about 20 mm and widths up to about 4 mm. Predictability of this type of installation in the anterior area of dental arches is now so good that the use of dental implants has entered the armamentarium of oral surgeons, prosthodontists and periodontists in the treatment of fully and partially edentulous patients. Attempts to install dental implants in posterior regions of the maxillary and mandibular arches have, however, encountered several unique problems.

On the one hand, such attempts have been frustrated by the presence of the inferior alveolar mandibular canal in the posterior mandible, and by the presence of the sinus cavities superior to the posterior maxillary bone. Risk of invading the sinus cavities and the mandibular canal is generally avoided, the result being that often in these posterior regions no more than about 8 mm or less of bone depth is available in which to bore a site to receive a dental implant fixture. Therefore, very short implants were placed with fewer cubic millimeters in bone for foundation. Lekholm reported reduced success with shorter implants. (2nd Int. Tissue International Congress, Rochester, Minn., Sept. 1990). In order to place longer implants in these regions, many surgeons have resorted to different surgical techniques, including sinus lift, bone augmentation and mandibular canal repositioning. These procedures are obviously of greater risk than standard implant treatment in the anterior regions of the mouth. It is an advantage of the present invention to avoid these procedures. Some practitioners have sought to overcome this problem in the mandible, if the mandibular canal is located in a buccal position, by installing an available dental implant fixture closer to the lingual surface, and thereby bypassing the mandibular canal, when adequate bone is available to the lingual surface to avoid the risk of fenestration. This procedure, when available, may have the advantage of providing partial primary stabilization in cortical bone, which is important for eventual osseointegration of the fixture with the bone.

It has become apparent that wider jawbones (as in the posterior regions) usually have more trabeculation and often are without adequate amounts of density of bone in their marrow spaces to provide anchorage for dental implants. In the maxillary and mandibular posterior regions the bone is cancellous internally and cortical externally, a condition sometimes termed "eggshell". It has been found to be often almost impossible to securely immobilize a dental implant in the marrow spaces of posterior jawbone regions. Jaffin & Berman noted less success in bone in posterior regions. J. Periodontal, 1991, 62:2–4. It has been suggested that the only hope of more predictable success in these cases is to place a dental implant so as to engage a denser, more cortical layer of bone that often protects the maxillary and nasal sinuses, or that covers the mandibular canal, all of which have inherent surgical risk. The above-described difficulties and proposed solutions are presented in greater detail in an article by Langer, B. et al entitled "Osseointegration: Its impact on the Interrelationships of Periodontics and Restorative Dentistry: Part 1: The International Journal of Periodontics & Restorative Dentistry, Volume 9, Number 2, 1989, at pages 85 to 105.

GENERAL NATURE OF THE INVENTION

In accordance with the present invention a dental implant having a cylindrically-shaped post portion which is preferably not more than about 13 mm long has a diameter large enough (about 5 or 6 mm) to make bone-to-implant contact with cortical bone at both the lingual and buccal sides of posterior "eggshell" jawbone without coming into contact with either the mandibular canal or the sinus floor. This new implant fixture has several advantages:

a—it has a length-to-width ratio in a range from about 0.833 to about 2.5 in dimensions providing bilateral bone-to-implant contact, without making contact with the mandibular canal or the sinus floor;

b—by contacting cortical bone at both sides of the bore in the jawbone it provides more complete initial stabilization to the installed dental implant; Langer et al., at page 89, show an installation in which a standard prior-existing long thin implant is located to engage lingual cortical plate to provide initial stabilization, which obviously does not provide this advantage; the installation is in an unfavorable position for the construction of a fixed prosthesis;

c—owing to its larger surface area it provides a more stable platform for molar restorations than is available from the prior existing narrower implant fixtures, as well as larger surface area of an implant contact with bone, which results in smaller actual stresses in the bone-implant interface under a given occlusal lcad; these advantage are also lacking in Langer et al. Although the reaction of bone to stresses imposed by occlusal loading on implant fixtures is not well known and understood, it appears reasonable that any loading in the posterior regions of the mouth where cancellous bone is prevalent would benefit from a wider distribution of these stresses in the cortical bone because of the ability of wider implant to engage both corticals.

d—non-circular (e.g.: hexagonal) manipulative and non-rotational devices now in use can be made wider to improve manipulation of the fixture and stabilization of restorations, especially single-tooth crowns, supported on them. In the existing state of the art with dental implant, the ratio of the width of the non-rotating feature to the total diameter of the implant is in a range of approximately 0.7 to 0.8 mm. Maintaining this same ratio in a larger diameter implant (5 or 6 mm in diameter, for example) obviously makes it possible to utilize a much larger dimension in the non-rotational features of the implant.

This larger dimension when used in conjunction with prosthetic components that have similar clearances or fit allowances between them as currently exist in the state of the art, provides for a much more stable interlocking mechanism. Essentially this revolves around the concept of retaining a minimum gap or fit between two components, but increasing the relative sizes of both of these components. By doing so, one allows the state of the art in existing manufacturing to be easily utilized to accomplish a more stable restoration when utilizing a larger diameter in the non-rotational dimensions of the components. By way of simple illustration, if one imagines a one-thousandth of an inch gap between an abutment and an implant fixture given the current state of the art, there will be a certain amount of play or micro movement between the prosthetic components and the implant fixture. If one can double the size of the non-rotational fitting, while still maintaining the same one-thousandth of an inch gap, the relative amount of motion or micro-movement between the prosthetic components and the implant fixture will decrease accordingly. The reduction of this relative motion is of significant advantage in keeping prosthetic components tight, particularly when used in single tooth applications.

In addition to the advantages offered by increased width of non-rotating fittings, the opportunity to increase the height or depth of such fittings may also offer significant advantages, particularly in single tooth restorations. The stability of the screw joint complex in single tooth restorations in the molar region is more important than in other regions of the mouth because of increased occlusal loads in this area. The addition of wider non-rotating features and taller or deeper non-rotating features, such as higher hexes or deeper hex sockets, will increase the integrity of the screw joint complex thereby reducing problems associated with micro movement and screw loosening.

e—Its larger size has advantages with regard to the final restoration and tooth emergence profile. Particularly in the posterior regions of the mouth where molars may be replaced, a larger diameter emergence profile may be desirable. This is particularly true in single tooth applications where it is important to preserve the emergence profile of a natural tooth in order to maintain subgingival contours which are easily cleaned and do not function as traps for debris and food. To create such tooth emergence profiles with smaller diameter implant fixtures often requires procedures such as ridge lapping or lingual bulking of restorative materials which makes hygiene very difficult. In anterior regions of the mouth it is often possible to overcome the shortcomings of narrower diameter implants by placing the implant more apically in the restored ridge. This allows for gradual contouring of the restoration subgingivally and can result in a more natural tooth emergence profile. However, in the posterior regions of the mouth this is often not practical because of limitations in anatomy which have been mentioned previously.

These and other advantages and features of the invention will become apparent from the following description of exemplary embodiments of the invention with reference to the accompanying drawings.

BRIEF DESCRIPTION OF THE DRAWINGS

FIG. 1 is a schematic view of the cross-section of a mandibular posterior region with a dental implant of the invention installed;

FIG. 1A is a schematic top view of FIG. 1;

FIG. 2 illustrates features of dental implants according to the invention;

FIG. 3 is a partial side view of an externally-threaded implant;

DETAILED DESCRIPTION OF THE DRAWINGS

Figure 5:
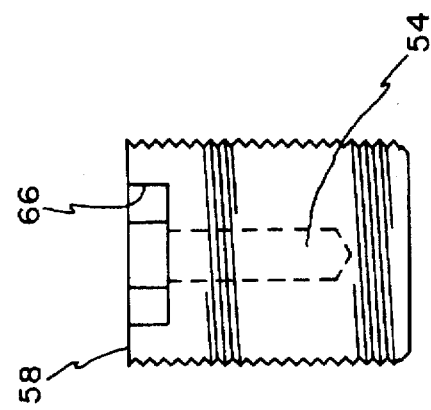
FIG. 5 is a side view of still another dental implant.

FIG. 1 represents a posterior region 10 of a mandible, showing a typical eggshell configuration which is cancellous internally 12 and cortical externally 14. The mandibular canal 16 is in the cancellous portion of the mandible. A dental implant 20 (shown more completely in FIG. 2) is installed in the mandible making partial bone-to-implant contact with the lingual and buccal cortical walls 14 at locations labelled 22, one of which is located in the superior cortex. For the most part, the implant displaces cancellous bone 12. The bone-to-implant contacts 22 provide near-total initial stabilization to the implant at both the lingual and the buccal sides of the mandible. The coronal opening through the superior cortex is not countersunk.

Referring now to FIG. 2, the implant of this invention has length L and width W dimensions which are unique and unlike the dimension of typical implants that are in regular current use. The ratio L/W is a range from about 0.833 to about 2.50. For example, L may be not more than 8 to 13 mm, while W may be up to about 7 or 8 mm, depending on the width of the jawbone at the posterior location chosen for the implant fixture. The limit on L is dictated by the location of the mandibular canal 16, which may be less than 8 or 10 mm.

In contrast to these unusual dimensions, implants currently available have lengths up to about 20 mm, and widths up to 4 mm, thus having L/W ratios as high as 4.5, for example. A dental implant having this L/W ratio and limited to L not greater than about 8 to 10 mm would not be able to make bone-to-implant contact with both sides of the cortical shell in a mandibular location.

FIG. 3 shows an implant 30 bearing screw threads 32 on its outer surface, for initial mechanical fixation of the implant in the coronal wall and in the cortical walls 14. In accordance with this embodiment the lower portion 34 of the implant body is tapered to a smaller diameter than the major portion of the implant body, but the peaks of the threads 32 are on a fixed cylindrical locus 36, so that the lower few threads 38 are deeper than all the others. This feature may be used when desired, in implants according to the present invention to provide deeper penetration of the threads into the cortical bone well within the jawbone and thereby enhance primary stabilization of the implant fixture in the cortical bone.

Figure 4A:
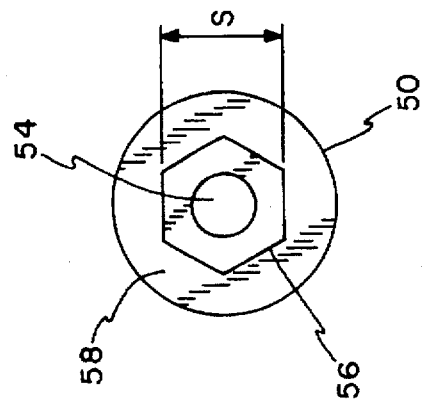
FIG. 4A is a top view of FIG. 4.
Figure 4:
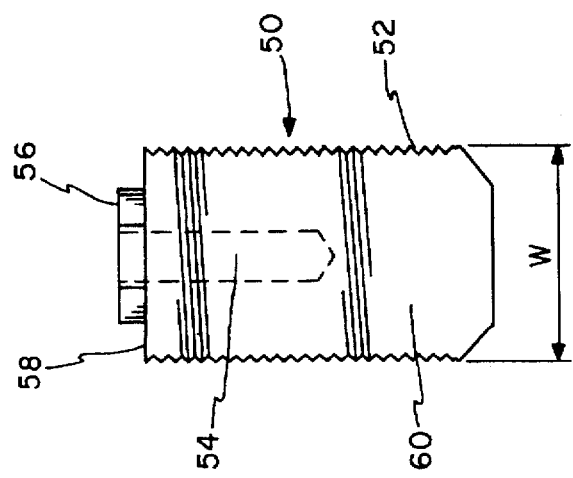
FIG. 4 is a side view of another externally-threaded.

FIGS. 4 and 4A show a cylindrical implant 50 bearing exterior screw threads 52 on a cylindrical body 60 of substantially uniform diameter W over its major portion lengthwise.

In common with prior existing implant, the implants of this invention may have a receiving bore 40 (in FIGS. 2 & 3; 54 in FIGS. 4 & 4A) for receiving and holding restoration components (not shown). This bore may be internally threaded as shown at 54 in FIG. 4. A non-circular (e.g: hexagonal) fitting 42 (FIG. 2), 56 (on top surface 58 in FIG. 4), may be provided, externally as shown in these figures, or internally 66 as shown in FIG. 5 for the known purposes of manipulation the implant and for stabilizing a restoration component against rotation with respect to the implant, around their common axis. The distance S between two opposite flat surfaces of this fitting may, however, be larger in the present invention than in the prior known implant fixtures, and ,the ratio between the width W and the dimension S can be selected to provide enhanced stabilization to the restoration components and to the restoration built on them, as is explained above in this specification.

Thus, for example, S can be greater than the usual 3 mm, while W can be up to about 10 mm. A dimension of S at 4 mm is closer to the diameter of a posterior tooth, and therefore more stabilizing. This yields a ratio of W/S that is 2.5. If S is still larger, this ratio becomes smaller.

We claim:

1. A dental implant designed and intended for installation in a posterior jawbone region that is normally the site of a molar-type tooth and is cancellous internally and cortical externally characterized by lingual and buccal cortical plates bounding a relatively large body of cancellous bone occupying a major portion of the labial-to-buccal thickness of said jawbone in said region, comprising:

an implant body having a gingival end with bone-engaging means on the exterior of said gingival end for fixing said implant in bone, said implant body having a width W at least as large as about 5.0 mm along substantially the entire length of the implant body for effecting bone-to-implant fixation between said implant and at least a portion of each of said plates simultaneously when said implant is installed in said site with said gingival end in the gingival region of said jawbone and with said implant body extending into said cancellous bone, said implant body having a threaded external side surface along substantially the entire length thereof to ensure threaded engagement with said cortical plates, said implant body having a length dimension L that is less than about 13 mm so as to stop short of the inferior alveolar mandibular canal if said site is in the posterior mandible and short of the superior sinus cavity if said site is in the posterior maxillary bone.

2. An implant according to claim 1 in which said width dimension W is about 6.0 mm.

3. An implant according to claim 1 in which said width dimension W is about 5.5 mm.

4. An implant according to claim 1 in which said gingival end includes a manipulating fitting.

5. An implant according to claim 4 in which said manipulating fitting is about 70% to about 80% of said width W.

6. An implant according to claim 1 in which said implant body is substantially a cylinder and has a substantially circular gingival surface at said gingival end.

7. An implant according to claim 6 in which the diameter of said cylinder is the same as said width dimension W.

8. An implant according to claim 6 in which said gingival surface is circular and a manipulating fitting is centered on said gingival surface.

9. An implant according to claim 8 in which the ratio of the diameter of said gingival surface to the cross-sectional dimension of said fitting is not larger than about 2.5.

10. The implant according to claim 1 in which said threaded external side surface includes threads extending into said gingival end.

11. An implant according to claim 10 in which said body is tapered to a smaller diameter close to said remote end of said fixture, and the peaks of said threads are on a constant diameter.

12. An implant according to claim 10 in which the diameter of said body is substantially constant throughout its axial length, and the peaks of said threads are on the locus of a larger coaxial cylinder.

13. An implant according to claim 1 in which the length dimension L of said fixture exceeds said width dimension W by an amount that is not more than about 2.5 times said width dimension W.

14. An implant according to claim 1 in which the ratio of the length dimension L of said fixture to said width dimension W is in a range from not more than one-to-one to less than about two and one-half-to-one.

15. In the beneficial use of a dental implant in a posterior region of a human maxillary or mandibular arch where the jawbone is cancellous internally and cortical externally and is characterized by lingual and buccal cortical plates bounding a mass of cancellous bone occupying a major portion of the buccal-to-lingual thickness of said jawbone and by the presence of the sinus cavities superior to the posterior maxillary bone or of the inferior alveolar mandibular canal in the posterior mandible, respectively, the improvement wherein the dental implant comprises:

an implant body of generally cylindrical form having a gingival end, an apical end, a substantially round transverse gingival surface at said gingival end, and threaded side surfaces extending substantially from said gingival end to said apical end, the diameter of said implant body being at least about 5.0 mm and being substantially constant along substantially the entire length of said implant body, and the length of said implant body between said gingival and apical ends being selected to be not more than about 2.5 times said diameter of said implant body so as to avoid contacting said sinus cavities or said mandibular canal with said apical end when said implant is installed with said gingival end substantially embraced within said jawbone.

16. The improvement according to claim 15 in which said diameter is about 5.5 mm.

17. The improvement according to claim 15 in which said diameter is about 6.0 mm.

18. The improvement according to claim 15 in which said length is selected to be not more than about 13 mm.

19. The improvement according to claim 15 wherein said threaded side surfaces include a thread extending into said gingival surface.

20. The improvement according to claim 15 in which said body is selected to include a manipulating fitting substantially centered on said gingival surface.

21. The improvement according to claim 20 in which the ratio of the diameter of said gingival surface to the cross-sectional dimension of said fitting is selected to be not larger than about 2.5.

22. The improvement according to claim 15 in which said body is selected to be tapered to a smaller diameter close to said apical end.

23. A method of installing a dental implant in a posterior region of a living human jawbone where said jawbone is cancellous internally and cortical externally and is characterized by lingual and buccal conical plates bounding a relatively large mass of cancellous bone occupying a major portion of the buccal-to-lingual thickness of said jawbone, comprising the steps of:

preparing an implant receiving bore in said jawbone at a selected site in said region, the diameter of said bore being large enough to reach both of said plates;

choosing an implant having a diameter W at least as large as the diameter of said bore and a length L stopping short of the inferior alveolar mandibular canal if said site is in the posterior mandible and short of the superior sinus cavity if said site is in the posterior maxillary bone, said implant having threads extending substantially along said length L; and installing said implant in said bore so as to make bone-to-implant contact with each of said plates and thereby to effect initial stabilization of said implant in said bore.

24. A dental implant for use in a human jawbone that is cancellous internally and cortical externally and is characterized by lingual and buccal cortical plates bounding a mass of cancellous bone occupying a major portion of the buccal-to-lingual thickness of said jawbone and by the presence of the sinus cavities superior to the posterior maxillary bone or of the inferior alveolar mandibular canal in the posterior mandible, respectively, said dental implant comprising:

- a body having a diametric width W of at least 5.0 mm and external threads extending substantially along the length of said body to be engaged with at least one of said cortical plates, said body having a gingival end with an upper surface and an apical end to be embedded into said jawbone; and
- a manipulating fitting on said upper surface of said gingival end, said fitting having a fitting width that is in the range from about 70% to about 80% of said diametric width W of said implant.

25. The implant of claim 24, wherein said fitting is a hexagonal boss and said fitting width is measured between said flats.

26. The implant of claim 24, wherein said fitting width is about 4.0 mm.

27. The implant of claim 24, wherein the distance from said fitting to a periphery of said body along said upper surface is approximately the same as the axial length of said fitting.

28. The implant of claim 27 wherein said manipulating fitting is an internal socket extending inwardly from said upper surface of said gingival end.

29. The implant of claim 24, wherein said diametric width W is about 5.5 mm.

30. The implant of claim 24, wherein said diametric width W is about 6.0 mm.

31. A dental implant designed and intended for installation in a posterior jawbone region that is normally the site of a molar-type tooth and is cancellous internally and cortical externally characterized by lingual and buccal cortical plates bounding a relatively large body of cancellous bone occupying a major portion of the labial-to-buccal thickness of said jawbone in said region, comprising:

- an implant body having a gingival end with bone-engaging means on the exterior of said gingival end for fixing said fixture in bone, said implant having a width W at least as large as about 4.5 mm along substantially the entire length of the implant, for effecting bone-to-implant fixation between said implant and at least a portion of each of said plates simultaneously when said implant is installed in said site with said gingival end in the gingival region of said jawbone and with said implant body extending into said cancellous bone, the external side surface of said implant being threaded along substantially the entire length of the implant to ensure threaded engagement with said cortical plates, said implant fixture having a length dimension L that is less than about 13 mm so as to stop short of the inferior alveolar mandibular canal if said site is in the posterior mandible and short of the superior sinus cavity if said site is in the posterior maxillary bone.

32. A dental implant for use in a human jawbone that is cancellous internally and cortical externally and is characterized by lingual and buccal cortical plates bounding a mass of cancellous bone occupying a major portion of the buccal-to-lingual thickness of said jawbone and by the presence of the sinus cavities superior to the posterior maxillary bone or of the inferior alveolar mandibular canal in the posterior mandible, respectively, said dental implant comprising:

- a body having a diametric width W of at least 4.5 mm and external threads extending substantially along the length of said body to be engaged with at least one of said cortical plates, said body having a gingival end with an upper surface and an apical end to be embedded into said jawbone; and
- a manipulating fitting on said upper surface of said gingival end, said fitting having a fitting width that is in the range from about 70% to about 80% of said diametric width W of said implant.

33. The implant of claim 32, wherein said fitting is a hexagonal boss and said fitting width is measured between said flats.

* * * * *

Disclaimer 5,709,547 - Richard J. Lazzara; Keith D. Beaty, both of West Palm Beach, Fla. DENTAL IMPLANT FOR ANCHORAGE IN CORTICAL BONE. Patent dated January 20, 1998. Disclaimer filed March 22, 1999, by the assignee, Implant Innovations, Inc.

Hereby enters this disclaimer to claims 1-33 of said patent.
*(Official Gazette, May 18, 1999)*